US012303232B2

(12) United States Patent
Wu et al.

(10) Patent No.: US 12,303,232 B2
(45) Date of Patent: May 20, 2025

(54) METHOD AND DEVICE FOR GENERATING PHOTOPLETHYSMOGRAPHY SIGNALS

(71) Applicant: Lepu Medical Technology (Beijing) Co., Ltd, Beijing (CN)

(72) Inventors: Zejian Wu, Shanghai (CN); Jun Cao, Beijing (CN)

(73) Assignee: Lepu Medical Technology (Beijing) Co., Ltd, Beijing (CN)

( * ) Notice: Subject to any disclaimer, the term of this patent is extended or adjusted under 35 U.S.C. 154(b) by 358 days.

(21) Appl. No.: 17/904,688

(22) PCT Filed: Nov. 18, 2020

(86) PCT No.: PCT/CN2020/129634
§ 371 (c)(1),
(2) Date: Aug. 19, 2022

(87) PCT Pub. No.: WO2021/164348
PCT Pub. Date: Aug. 26, 2021

(65) Prior Publication Data
US 2023/0071469 A1 Mar. 9, 2023

(30) Foreign Application Priority Data
Feb. 21, 2020 (CN) .......................... 202010110280.7

(51) Int. Cl.
*G06K 9/40* (2006.01)
*A61B 5/00* (2006.01)
*A61B 5/02* (2006.01)

(52) U.S. Cl.
CPC .............. *A61B 5/0059* (2013.01); *A61B 5/02* (2013.01); *A61B 5/7203* (2013.01)

(58) Field of Classification Search
CPC ....... A61B 5/0059; A61B 5/02; A61B 5/7203; A61B 5/0077; A61B 5/7225;
(Continued)

(56) References Cited

U.S. PATENT DOCUMENTS

2015/0148687 A1  5/2015  Kitajima et al.
2016/0302674 A1 10/2016  Moyer et al.
(Continued)

FOREIGN PATENT DOCUMENTS

CN  104639799 B  10/2017
CN  105395184 B   5/2018
(Continued)

OTHER PUBLICATIONS

International Search Report for Application No. PCT/CN2020/129634 dated Feb. 19, 2021, 2 pages.
(Continued)

*Primary Examiner* — Duy M Dang
(74) *Attorney, Agent, or Firm* — TraskBritt (57) ABSTRACT

A method for generating PPG signals may include sequentially performing single-frame red and green channel data calculation on all skin surface video data frame images of a frame image sequence of skin surface video data according to preset red and green light pixel threshold ranges to generate first red and green light signals; performing signal band-pass filtering preprocessing on the first red and green light signals to generate second red and green light digital signals; obtaining a preset signal determination identifier; determining whether to perform signal maximum frequency difference determination on the second red light signal and the second green light signal, and generating a first determination result; when the first determination result is an up-to-standard signal identifier, performing signal-to-noise ratio determination on the second red and/or green light signal to generate a second determination result; and when the second determination result is the up-to-standard signal identifier, generating a PPG signal.

14 Claims, 3 Drawing Sheets

(58) Field of Classification Search
CPC ....... A61B 5/02416; G06T 5/00; G06T 5/006;
G06T 5/10; G06T 5/20; G06T
2207/20172; G06T 5/50; G06T 5/40;
G06T 2207/20212; G06T 2207/20216;
G06T 2207/20221; G06T 2207/20224
See application file for complete search history.

(56) References Cited

U.S. PATENT DOCUMENTS

| | | |
|---|---|---|
| 2017/0007185 A1 | 1/2017 | Lin et al. |
| 2018/0214088 A1 | 8/2018 | Newberry |
| 2018/0360330 A1 | 12/2018 | Pearce et al. |
| 2019/0050985 A1* | 2/2019 | Den Brinker ........ A61B 5/0261 |
| 2022/0265150 A1* | 8/2022 | De Haan ............ A61B 5/14551 |

FOREIGN PATENT DOCUMENTS

| | | |
|---|---|---|
| CN | 111297339 B | 7/2022 |
| EP | 3207862 A1 | 8/2017 |

OTHER PUBLICATIONS

International Written Opinion for Application No. PCT/CN2020/129634 dated Feb. 19, 2021, 5 pages.
Chinese Notice of Allowance for Chinese Application No. 202010110280.7, dated Jun. 28, 2022, 3 pages with translation.
European Search Report for Application No. 20920454.4 dated Jul. 5, 2023, 8 pages.

* cited by examiner

1. Call a video recording device to perform a continuous acquisition and photographing operation on a local skin surface of a living body with a preset acquisition time threshold as a photographing time duration to generate skin surface video data, and perform frame image extraction on the skin surface video data to generate a skin surface video data frame image sequence 2. Sequentially perform single-frame red channel data calculation on all skin surface video data frame images of the skin surface video data frame image sequence according to a preset red light pixel threshold range to generate a first red light digital signal, and sequentially perform single-frame green channel data calculation on all the skin surface video data frame images of the skin surface video data frame image sequence according to a preset green light pixel threshold range to generate a first green light digital signal 3. Perform signal band-pass filtering preprocessing on the first red light digital signal according to a preset band-pass filtering frequency threshold range to generate a second red light digital signal, and perform signal band-pass filtering preprocessing on the first green light digital signal according to the preset band-pass filtering frequency threshold range to generate a second green light digital signal 4. Obtain a preset signal determination identifier 5. Determine, according to the signal determination identifier, whether to perform signal maximum frequency difference determination on the second red light digital signal and the second green light digital signal, perform the signal maximum frequency difference determination on the second red light digital signal and the second green light digital signal to generate a first determination result when the signal determination identifier is the red and green light dual detection identifier, or directly set the first determination result as an up-to-standard signal identifier when the signal determination identifier is the red light single detection identifier 6. Perform, when the first determination result is the up-to-standard signal identifier, signal-to-noise ratio determination on the second red light digital signal and/or the second green light digital signal according to the signal determination identifier to generate a second determination result 7. Perform, when the second determination result is the up-to-standard signal identifier, PPG signal generation on the second red light digital signal and/or the second green light digital signal according to the signal determination identifier to generate a PPG signal

METHOD AND DEVICE FOR GENERATING PHOTOPLETHYSMOGRAPHY SIGNALS

CROSS-REFERENCE TO RELATED APPLICATIONS

This application is a national phase entry under 35 U.S.C. § 371 of International Patent Application PCT/CN2020/129634, filed Nov. 18, 2020, designating the United States of America and published as International Patent Publication WO 2021/164348 A1 on Aug. 26, 2021, which claims the benefit under Article 8 of the Patent Cooperation Treaty to Chinese Patent Application Serial No. 202010110280.7, filed Feb. 21, 2020.

TECHNICAL FIELD

The disclosure relates to the technical field of electrophysiological signal processing, in particular, to a method and device for generating Photoplethysmography (PPG) signals.

BACKGROUND

The work condition of the heart is affected by many factors such as the current health, hormone level, emotional state and even life style of people, and conversely, the health and disease information of people can be obtained by analyzing the motion trajectory of the heart. To obtain motion trajectory data of the heart, it is necessary to monitor heart motions and acquire heart data, which are traditionally completed through an electrocardiogram (ECG) monitoring technique. By adoption of this technique, lead electrodes are connected to multiple parts of the human body to acquire ECG signals. During specific operation, a monitored object has to lie still or wear multiple contact devices (heart patches, heart belts, or the like) all the time in daily life, which causes much inconvenience to the activities and normal life of the monitored object.

Photoplethysmography (PPG) is a non-invasive detection method for detecting the change of blood volume in viable tissues through a photoelectric method. When the heart beats, the blood flow in unit area in blood vessels changes periodically, the blood volume changes correspondingly, and a PPG signal reflecting the light absorption capacity of blood also changes periodically. The PPG signal may be acquired by measuring the fingers, ears or other parts. A series of oriented analysis of heart activities may be carried out through the PPG signals, and compared with the ECG method, the PPG method may improve the comfort of the monitored object. However, in actual application, existing PPG signal acquisition devices and methods are found to be inflexible: only a red light source or an infrared light source may be used as a radiation source, an acquisition front end is generally a customized mechanical device such as a finger clip or an ear clip, and acquired data have to be analyzed through specific sensors. All these problems make it more difficult to acquire PPG signal data through an upper medical application.

BRIEF SUMMARY

The objective of the disclosure is to overcome the defects of the prior art by providing a method and device for generating PPG signals. According to the method and device, the type of a radiation source is not specified, so common lamplight may be adopted; a PPG signal front-end acquisition device is simplified, and a common mobile terminal may be used; recorded video data is analyzed to generate a PPG signal, which not only meets the requirements for real-time analysis and data backup of local equipment, but also meets the requirements for remote transmission and analysis; valid signals may be recognized independent of specific sensors, so the PPG data acquisition difficult is lowered for an application layer; and a signal determination identifier is set to improve the compatibility with various photographing devices.

To fulfill the above objective, in a first aspect, the embodiments of the disclosure provide a method for generating PPG signals, comprising:

Sequentially performing single-frame red channel data calculation on all skin surface video data frame images of a skin surface video data frame image sequence according to a preset red light pixel threshold range to generate a first red light digital signal, and sequentially performing single-frame green channel data calculation on all the skin surface video data frame images of the skin surface video data frame image sequence according to a preset green light pixel threshold range to generate a first green light digital signal, wherein the skin surface video data frame image sequence comprises multiple skin surface video data frame images;

Performing signal band-pass filtering preprocessing on the first red light digital signal according to a preset band-pass filtering frequency threshold range to generate a second red light digital signal, and performing signal band-pass filtering preprocessing on the first green light digital signal according to the preset band-pass filtering frequency threshold range to generate a second green light digital signal;

Obtaining a preset signal determination identifier, wherein the signal determination identifier is a red and green light dual detection identifier or a red light single detection identifier;

Determining, according to the signal determination identifier, whether to perform signal maximum frequency difference determination on the second red light digital signal and the second green light digital signal, performing the signal maximum frequency difference determination on the second red light digital signal and the second green light digital signal to generate a first determination result when the signal determination identifier is the red and green light dual detection identifier, or directly setting the first determination result as an up-to-standard signal identifier when the signal determination identifier is the red light single detection identifier;

Performing, when the first determination result is the up-to-standard signal identifier, signal-to-noise ratio determination on the second red light digital signal and/or the second green light digital signal according to the signal determination identifier to generate a second determination result; and Performing, when the second determination result is the up-to-standard signal identifier, PPG signal generation on the second red light digital signal and/or the second green light digital signal according to the signal determination identifier to generate a PPG signal.

Preferably, the frame image sequence of skin surface video data is generated by calling a video recording device to perform a continuous acquisition and photographing operation on a local skin surface of a living body with a preset acquisition time threshold as a photographing time duration to generate skin surface video data and then performing frame image extraction on the skin surface video data.

Further, calling a video recording device to perform a continuous acquisition and photographing operation on a local skin surface of a living body with a preset acquisition time threshold as a photographing time duration to generate skin surface video data specifically comprises:

Calling an illuminating module of the video recording device to provide illumination for the local skin surface of the living body, wherein the video recording device comprises the illuminating module and a video recording module, and the video recording module at least comprises a lens module;

When a physical distance between the illuminating module and the lens module is less than or equal to a preset device distance threshold, covering the illuminating module and the lens module with the local skin surface of the living body; or, when the physical distance between the illuminating module and the lens module is greater than the device distance threshold, covering the lens module with the local skin surface of the living body; and Calling the video recording module to perform the continuous acquisition and photographing operation on the local skin surface of the living body with the preset acquisition time threshold as the photographing time duration to generate the skin surface video data.

Further, the method further comprises:

In the process of calling the video recording device to perform the continuous acquisition and photographing operation on the local skin surface of the living body with the preset acquisition time threshold as the photographing time duration, performing continuous video fragment extraction on the video data acquired and photographed by the video recording device with a preset cached fragment time threshold as a fragment extraction length to generate multiple cached fragments;

Extracting frame images from the cached fragments and sorting all the extracted frame images in chronological order to generate a cached fragment frame image sequence, wherein the cached fragments comprise multiple frame images;

Performing red pixel proportion statistics on all cached fragment frame images of the cached fragment frame image sequence according to the red light pixel threshold range to generate a red proportion parameter, and performing noise pixel proportion statistics according to a preset noise pixel threshold range to generate a noise proportion parameter, wherein the cached fragment frame image sequence comprises multiple cached fragment frame images;

Performing out-of-skin surface photographing error recognition determination on the catching fragments according to the red proportion parameter, and when the red proportion parameter is less than a preset red proportion lower threshold, stopping the continuous acquisition and photographing operation, and generating out-of-skin surface photographing error information; and Performing out-of-skin surface photographing error recognition determination on the cached fragments according to the noise proportion parameter, and when the noise proportion parameter is greater than a preset noise proportion upper threshold, stopping the continuous acquisition and photographing operation, and generating the out-of-skin surface photographing error information.

Preferably,

The first determination result is the up-to-standard signal identifier or a not-up-to-standard signal identifier;

The second determination result is the up-to-standard signal identifier or the not-up-to-standard signal identifier.

Preferably, the step of sequentially performing single-frame red channel data calculation on all skin surface video data frame images of a skin surface video data frame image sequence according to a preset red light pixel threshold range to generate a first red light digital signal, and sequentially performing single-frame green channel data calculation on all the skin surface video data frame images of the skin surface video data frame image sequence according to a preset green light pixel threshold range to generate a first green light digital signal specifically comprises:

Step 61, initializing a temporary first red light digital signal to be null, initializing a temporary first green light digital signal to be null, initializing a first index to 1, and initializing a first total number to a total number of the skin surface video data frame images of the skin surface video data frame image sequences;

Step 62, extracting the skin surface video data frame image corresponding to the first index from the skin surface video data frame image sequence to generate a first-index skin surface video data frame image;

Step 63, collecting all pixels, meeting the red light pixel threshold range, in the first-index skin surface video data frame image according to the red light pixel threshold range to generate a red pixel set, and performing weighted average calculation on pixel values of all the pixels in the red pixel set through a designated weighted average method to generate first-index frame red channel data; and adding the first-index frame red channel data into the temporary first red light digital signal as red light signal point data;

Step 64, collecting all pixels, meeting the green light pixel threshold range, in the first-index skin surface video data frame image according to the green light pixel threshold range to generate a green pixel set, and performing weighted average calculation on pixel values of all the pixels in the green pixel set through a designated weighted average method to generate first-index frame green channel data; and adding the first-index frame green channel data into the temporary first green light digital signal as green light signal point data;

Step 65, increasing the first index by 1;

Step 66, determining whether the first index is greater than the first total number; if the first index is less than or equal to the first total number, performing Step 62; or, if the first index is greater than the first total number, performing Step 67; and Step 67, setting the first red light digital signal as the temporary first red light digital signal; and setting the first green light digital signal as the temporary first green digital signal.

Preferably, the step of performing signal band-pass filtering preprocessing on the first red light digital signal according to a preset band-pass filtering frequency threshold range to generate a second red light digital signal, and performing signal band-pass filtering preprocessing on the first green light digital signal according to the preset band-pass filtering frequency threshold range to generate a second green light digital signal specifically comprises:

According to the band-pass filtering frequency threshold range, performing digital signal filtering processing on low-frequency noise signal points with a signal frequency lower than the band-pass filtering frequency threshold range and high-frequency noise signal points with a signal frequency higher than the band-pass filtering frequency threshold range in the first red light digital signal to generate the second red light digital signal; and According to the band-pass filtering frequency threshold range, performing digital signal filtering processing on low-frequency noise signal points with a signal frequency lower than the band-pass filtering frequency threshold range and high-frequency noise signal points with a signal frequency higher than the band-pass filtering frequency threshold range in the first green light digital signal to generate the second green light digital signal.

Preferably, the step of determining, according to the signal determination identifier, whether to perform signal maximum frequency difference determination on the second red light digital signal and the second green light digital signal, performing the signal maximum frequency difference determination on the second red light digital signal and the second green light digital signal to generate a first determination result when the signal determination identifier is the red and green light dual detection identifier, or directly setting the first determination result as an up-to-standard signal identifier when the signal determination identifier is the red light single detection identifier specifically comprises:

Step 81, initializing a temporary first determination result to be null;

Step 82, determining whether the signal determination identifier is the red and green light dual detection identifier; when the signal determination identifier is the red and green light dual detection identifier, performing Step 83; or, when the signal determination identifier is not the red light single detection identifier, performing Step 85;

Step 83, performing digital signal time domain-frequency domain conversion on the second red light digital signal through discrete Fourier transform to generate a red light frequency domain signal, and performing digital signal time domain-frequency domain conversion on the second green light digital signal through discrete Fourier transform to generate a green light frequency domain signal; extracting an maximum-energy frequency from the red light frequency domain signal to generate a maximum red light frequency, and extracting an maximum-energy frequency from the green light frequency domain signal to generate a maximum green light frequency; and generating a maximum red-green frequency difference according to a frequency difference between the maximum red light frequency and the maximum green light frequency;

Step 84, performing signal maximum frequency difference determination on the maximum red-green frequency difference according to a preset maximum frequency difference threshold range; when the maximum red-green frequency difference does not exceed the maximum frequency difference threshold range, setting the temporary first determination result as the up-to-standard signal identifier; or, when the maximum red-green frequency difference exceeds the maximum frequency difference threshold range, setting the temporary first determination result as the not-up-to-standard signal identifier; and performing Step 86;

Step 85, setting the temporary first determination result as the up-to-standard signal identifier; and Step 86, setting the first determination result as the temporary first determination result.

Preferably, the step of performing, when the first determination result is the up-to-standard signal identifier, signal-to-noise ratio determination on the second red light digital signal and/or the second green light digital signal according to the signal determination identifier to generate a second determination result specifically comprises:

Step 90, initializing a temporary second determination result to be null;

Step 91, when the first determination result is the up-to-standard signal identifier, performing determination according to the signal determination identifier; when the signal determination identifier is the red and green light dual detection identifier, performing Step 92; or, when the signal determination identifier is the red light single detection identifier, performing Step 95;

Step 92, performing multi-order Butterworth band-stop filtering processing on the second red light digital signal according to a preset band-stop filtering frequency threshold range, and filtering valid signals with a signal frequency meeting the band-stop filtering frequency threshold range out of the second red light digital signal to generate a red light noise signal; and performing multi-order Butterworth band-stop filtering processing on the second green light digital signal according to the preset band-stop filtering frequency threshold range, and filtering valid signals with a signal frequency meeting the band-stop filtering frequency threshold range out of the second green light digital signal to generate a green light noise signal;

Step 93, calculating signal energy of the second red light digital signal to generate red light signal energy, calculating signal energy of the red light noise signal to generate red light noise energy, generating valid red light signal energy according to a difference between the red light signal energy and the red light noise energy, and generating a red light signal-to-noise ratio according to a ratio of the valid red light signal energy to the red light noise energy; calculating signal energy of the second green light digital signal to generate green light signal energy, calculating signal energy of the green light noise signal to generate green light noise energy, generating valid green light signal energy according to a difference between the green light signal energy and the green light noise energy, and generating a green light signal-to-noise ratio according to a ratio of the valid green light signal energy to the green light noise energy;

Step 94, if the red light signal-to-noise ratio and the green light signal-to-noise ratio are both less than a preset signal-to-noise threshold, setting the temporary second determination result as the not-up-to-standard signal identifier; or, if any one of the red light signal-to-noise ratio and the green light signal-to-noise ratio is greater than or equal to the signal-to-noise threshold, setting the temporary second determination result as the up-to-standard signal identifier; and performing Step 97;

Step 95, performing multi-order Butterworth band-stop filtering processing on the second red light digital signal according to the band-stop filtering frequency threshold range, filtering valid signals with a signal frequency meeting the band-stop filtering frequency threshold range out of the second red light digital signal to generate the red light noise signal; calculating the signal energy of the second red light digital signal to generate the red light signal energy, calculating the signal energy of the red light noise signal to generate the red light noise energy, generating the valid red light signal energy according to the difference between the red light signal energy and the red light noise energy, and generating the red light signal-to-noise ratio according to the ratio of the valid red light signal energy to the red light noise energy;

Step 96, if the red light signal-to-noise ratio is less than the signal-to-noise threshold, setting the temporary second determination result as the not-up-to-standard signal identifier; or, if the red light signal-to-noise ratio is greater than or equal to the signal-to-noise threshold, setting the temporary second determination result as the up-to-standard signal identifier; and Step 97, setting the second determination result as the temporary second determination result.

Preferably, the step of performing, when the second determination result is the up-to-standard signal identifier, PPG signal generation on the second red light digital signal and/or the second green light digital signal according to the signal determination identifier to generate a PPG signal specifically comprises:

When the second determination result is the up-to-standard signal identifier, setting the PPG signal to be null, initializing a channel identifier of the PPG signal to be null, initializing a red light digital signal of the PPG signal to be null, and initializing a green light digital signal of the PPG signal to be null;

When the signal determination identifier is the red and green light dual detection identifier, setting the channel identifier of the PPG signal as a red and green channel identifier, setting the red light digital signal of the PPG signal as the second red light digital signal, and setting the green light digital signal of the PPG signal as the second green light digital signal; or When the signal determination identifier is the red light single detection identifier, setting the channel identifier as a red channel identifier, and setting the red light digital signal of the PPG signal as the second red light digital signal.

Preferably, the method further comprises:

When the first determination result is the not-up-to-standard signal identifier, stopping the PPG signal generation, and generating signal quality error information; and When the second determination result is the not-up-to-standard signal identifier, stopping the PPG signal generation, and generating signal quality error information.

According to the method for generating PPG signals provided in the first aspect of the embodiments of the disclosure, the type of a radiation source is not specified, so common lamplight may be adopted; a PPG signal front-end acquisition device is simplified, and a common mobile terminal may be used; recorded video data is analyzed to generate a PPG signal, which not only meets the requirements for real-time analysis and data backup of local equipment, but also meets the requirements for remote transmission and analysis; valid signals may be recognized independent of specific sensors, so the PPG data acquisition difficult is lowered for an application layer; and a signal determination identifier is set to improve the compatibility with various photographing devices.

In a second aspect, the embodiments of the disclosure provide equipment, comprising a memory and a processor, wherein the memory is used to store a program, and the processor is used to implement the method in the first aspect and in all implementations of the first aspect.

In a third aspect, the embodiments of the disclosure provide a computer program product comprising instructions, wherein the computer program product enables a computer to implement the method in the first aspect and in all implementations of the first aspect when running on the computer.

In a fourth aspect, the embodiments of the disclosure provide a computer-readable storage medium having a computer program stored therein, wherein when the computer program is executed by a processor, the method in the first aspect and in all implementations of the first aspect is implemented.

BRIEF DESCRIPTION OF THE DRAWINGS

FIG. 1 is a schematic diagram of a method for generating PPG signals according to Embodiment 1 of the disclosure;

DETAILED DESCRIPTION

To gain a better understanding of the purposes, technical solutions and advantages of the disclosure, the disclosure will be described in further detail below in conjunction with the accompanying drawings. Obviously, the embodiments in the following description are merely illustrative ones, and are not all possible ones of the disclosure. All other embodiments obtained by those ordinarily skilled in the art according to the following ones without creative labor should also fall within the protection scope of the disclosure.

Before the disclosure is expounded in further detail with reference to embodiments, some technical means involved in this specification will be briefly introduced below.

Conventionally, a PPG signal is acquired as follows: the skin surface is irradiated with a specific light source, and then a light signal reflected or transmitted by the skin surface is received by a specific light receiving sensor; and an analysis module of the sensor records and analyzes light intensity changes in chronological order to finally represent dynamic pulse waves by a normalized PPG signal.

With reference to the PPG signal analysis principle, it is found that, in the continuous heartbeat process, the skin surface of a test subject absorbs the energy of red light and green light in natural light in the same trend as a specific light source of a conventional PPG acquisition device. So, other media may be used to obtain the normalized PPG signal as long as the media can reflect the change trend of red and green light on the skin surface within a time period.

Based on the above finding, different from conventional PPG signal acquisition devices, the embodiments of the disclosure have no specific light requirements, do not irradiate the skin surface with a specific light source and do not acquire the light intensity with a specific sensor. In the embodiments of the disclosure, natural light is adopted (even if a strong light source such as a flashlight is used, the strong light source is merely used to increase the light intensity rather than specifying the light property), a common photographing device (such as a camera of a mobile terminal) is used to photograph a designated skin surface (such as the finger, the earlobe, the neck or the forehead) of the test subject, and frame images are extracted from acquired video data to generate a frame image sequence. In the embodiments of the disclosure, these continuous frame images are used as a medium to capture the change trend of red and green light, which is specifically implemented as follows: weighted statistics is performed on red and green pixel values in each frame image to generate original red and green signal points of the frame image at a corresponding time, and corresponding filtering and denoising processing is performed on the original red and green signals to generate red and green data channel values of the PPG signal. The embodiments of the disclosure provide an approach for ensuring the compatibility with the photographing device: signal determination identifier (including red and green light dual detection identifier and red light single detection identifier). When the lens of the photographing device has an obvious green light refraction defect, the red and green single detection identifier is selected form a PPG signal only with reference to red light. When the lens of the photographing device does not have an obvious refraction defect, the red and green dual detection identifier is selected to form a PPG signal with reference to red and green light signals.

As shown in FIG. 1, which is a schematic diagram of a method for generating PPG signals according to Embodiment 1 of the disclosure, the method comprises the following steps:

Step 1, a video recording device is called to perform a continuous acquisition and photographing operation on a local skin surface of a living body with a preset acquisition time threshold as a photographing time duration to generate skin surface video data; and frame image extraction is performed on the skin surface video data to generate a frame image sequence of skin surface video data;

Wherein, the frame image sequence of skin surface video data comprises multiple frame images of skin surface video data;

Step 1 comprises: Step 11, an illuminating module of the video recording device is called to provide illumination for the local skin surface of the living body;

Wherein, the video recording device comprises the illuminating module and a video recording module, and the video recording module at least comprises a lens module;

Here, any mobile terminals provided with a camera and having a video recording function in daily life may be used as the video recording device in this embodiment of the disclosure; and before photographing, a flashlight of the mobile terminal is turned on and is kept on normally to meet the requirement for a stable illuminating light source;

Step 12, when a physical distance between the illuminating module and the lens module is less than or equal to a preset device distance threshold, both the illuminating module and the lens module are covered with the local skin surface of the living body; or, when the physical distance between the illuminating module and the lens module is greater than the device distance threshold, only the lens module is covered with the local skin surface of the living body;

Here, during photographing, the local skin surface of the photographed living body should be slightly pressed against the camera of the mobile terminal; if the flashlight and the camera of the mobile terminal are close to each other, the skin surface covers both the flashlight and the camera; or, if the flashlight and the camera of the mobile terminal are away from each other, the skin surface only covers the camera; and in the photographing process, the skin surface should be kept static, and force should be applied uniformly to the skin surface.

Step 13, the video recording module is called to perform the continuous acquisition and photographing operation on the local skin surface of the living body with the preset acquisition time threshold as the photographing time duration.

Here, the acquisition time threshold may be predefined repeatedly according to the data storage capacity and analysis capacity of an actual application.

Here, the local skin surface of the living body may be the fingertip, the earlobe, the forehead, or the like. In principle, any skin surfaces with a good transmission or reflection effect may be used.

Here, in Embodiment 1, when the video recording module is called to perform the continuous acquisition and photographing operation on the local skin surface of the living body with the preset acquisition time threshold as the photographing time duration, continuous video fragment extraction is performed on the video data acquired and photographed by the video recording device with a preset caching fragment time threshold as a fragment extraction length to generate multiple cached fragments. For example, assume the acquisition time threshold is 5 min and the caching fragment time threshold is 1 s, a video recorded in each is in the 5 min photographing process is stored as a cached fragment, and cached data is further analyzed;

Further, in Embodiment 1, frame images are extracted from the cached fragments, and all the extracted frame images are sorted in chronological order to generate a cached fragment frame image sequence; red pixel proportion statistics is performed on all cached fragment frame images of the cached fragment frame image sequence according to a red light pixel threshold range to generate a red proportion parameter, and noise pixel proportion statistics is performed according to a preset noise pixel threshold range to generate a noise proportion parameter. Assume the is video comprises 24 frames, it indicates that each cached fragment frame image sequence comprises 24 cached fragment frame images. Here, assume the skin surface completely covers the camera lens in the photographing process, most pixels in the frame images of the video will be red pixels. Otherwise, if the skin surface is not pressed against the camera lens or is moved away from the camera lens, the number of red pixels will be decreased, the number of noise pixels will be increased, and in this case, the red proportion parameter and the noise proportion parameter of each cached fragment frame image should be calculated and compared;

Finally, determination for error recognition of out-of-skin surface photographing is performed on each cached fragment, and when the red proportion parameter is less than a preset red proportion lower threshold, the continuous acquisition and photographing operation is stopped, and error information for out-of-skin surface photographing is generated; and when the noise proportion parameter is greater than a preset noise proportion upper threshold, the continuous acquisition and photographing operation is stopped, and the error information for out-of-skin surface photographing is generated. When such an error occurs, the mobile terminal may be required to remind users to re-photograph the skin surface manually or automatically according to the error information, based on actual application requirements of an upper application.

Step 2, single-frame red channel data calculation is sequentially performed on all the frame images of skin surface video data in the frame image sequence of skin surface video data according to a preset red light pixel threshold range to generate a first red light digital signal, and single-frame green channel data calculation is sequentially performed on all the frame images of skin surface video data in the frame image sequence of skin surface video data according to a preset green light pixel threshold range to generate a first green light digital signal;

Step 2 comprises: Step 21, a temporary first red light digital signal is initialized to be null, a temporary first green light digital signal is initialized to be null, a first index is initialized to 1, and a first total number is initialized to a total number of the frame images of skin surface video data of the frame image sequence of skin surface video data s;

Step 22, the skin surface video data frame image corresponding to the first index is extracted from the frame image sequence of skin surface video data to generate a first-index skin surface video data frame image;

Step 23, all pixels, meeting the red light pixel threshold range, in the first-index skin surface video data frame image are collected according to the red light pixel threshold range to generate a red pixel set, and weighted average calculation is performed on pixel values of all the pixels in the red pixel set through a designated weighted average method to generate first-index frame red channel data; and the first-index frame red channel data is added into the temporary first red light digital signal as red light signal point data;

Here, the designated weighted average method is generally a sum average method. For example, all pixels, meeting the red light pixel threshold range, in a frame image of first skin surface video data are extracted to generate a red pixel total number (because the degrees of reflection and transmission of different parts under the irradiation of a light source are different due to their internal structure or blood vessels, the light transmittances will be different, the shades of red pixels in the recorded video will also be different, so the pixel threshold range is adopted), and the sum of pixel values of all the pixels, meeting the red light pixel threshold range, in the first skin surface video data frame image is calculated to generate a red pixel value sum, and the first-index frame red channel data=the red pixel value sum/the red pixel total number;

Step 24, all pixels, meeting the green light pixel threshold range, in the frame image of first-index skin surface video data are collected according to the green light pixel threshold range to generate a green pixel set, and weighted average calculation is performed on pixel values of all the pixels in the green pixel set through a designated weighted average method to generate first-index frame green channel data; and the first-index frame green channel data is added into the temporary first green light digital signal as green light signal point data;

Here, the designated weighted average method is a conventional sum average method, so the first-index frame green channel data=green pixel value sum/green pixel total number;

Step 25, the first index is increased by 1;

Step 26, whether the first index is greater than the first total number is determined; if the first index is less than or equal to the first total number, Step 22 is performed; or, if the first index is greater than the first total number, Step 27 is performed;

Step 27, the first red light digital signal is set as the temporary first red light digital signal, and the first green light digital signal is set as the temporary first green digital signal.

Step 2 is expounded in further detailed in Step 21 to Step 27. In Embodiment 1, information of various lights (red light and green light in this embodiment) in all the frame images in the frame image sequence converted from skin surface video data is extracted in Step 2; as for the extraction of light signals, weighted average calculation is performed on specific pixels in the frame image to obtain a pixel average that is used to represent the color channel data of the corresponding light in the frame image; and each frame image in the video is processed in the same way in chronological order to obtain two sets of one-dimensional digital signals: first red light digital signal and first green light digital signal.

Step 3, signal band-pass filtering preprocessing is performed on the first red light digital signal according to a preset band-pass filtering frequency threshold range to generate a second red light digital signal, and signal band-pass filtering preprocessing is performed on the first green light digital signal according to the preset band-pass filtering frequency threshold range to generate a second green light digital signal;

Step 3 comprises: Step 31, according to the band-pass filtering frequency threshold range, digital signal filtering processing is performed on low-frequency noise signal points with a signal frequency lower than the band-pass filtering frequency threshold range and high-frequency noise signal points with a signal frequency higher than the band-pass filtering frequency threshold range in the first red light digital signal to generate the second red light digital signal; and Step 32, according to the band-pass filtering frequency threshold range, digital signal filtering processing is performed on low-frequency noise signal points with a signal frequency lower than the band-pass filtering frequency threshold range and high-frequency noise signal points with a signal frequency higher than the band-pass filtering frequency threshold range in the first green light digital signal to generate the second green light digital signal.

Here, Step 3 is further expounded in Step 31 to Step 32. In Step 3, signal preprocessing, namely denoising, is performed on the two light digital signals extracted according to the video data. In Embodiment 1, band-pass filtering is used for denoising, that is, a band-pass filtering frequency threshold range is preset, and signals, interference and noise lower or higher than the band-pass filtering frequency threshold range are restrained based on the band-pass filtering principle. Generally, the band-pass filtering frequency threshold range is 0.5-10 THz. When some mobile terminals are used for band-pass filtering, considering the processing capacity of the mobile terminals, a finite impulse response (FIR) filtering module is used.

Step 4, a preset signal determination identifier is obtained;

Wherein, the preset signal determination identifier is a red and green light dual detection identifier or a red light single detection identifier.

Herein, the signal determination identifier is set and determined for the purpose of improving the compatibility with the photographing device. In some specific application scenarios, some mobile terminals have a poor capacity to process green light due to poor lens quality, equipment aging, an undeveloped polarization algorithm or other reasons, a sufficient quantity of pixel information with pixel values up to standard cannot be obtained from video data and even frame image data of videos acquired through these mobile terminals, and thus, a green light digital signal cannot be generated. In this case, the signal determination identifier is set to handle different cases flexibly: red and green light dual detection means that both red and green signals need to be recognized, and red light single detection means that only a red light signal needs to be recognized.

Step 5, whether to perform signal maximum frequency difference determination on the second red light digital signal and the second green light digital signal is determined according to the signal determination identifier, the signal maximum frequency difference determination is performed on the second red light digital signal and the second green light digital signal to generate a first determination result when the signal determination identifier is the red and green light dual detection identifier, or the first determination result is directly set as an up-to-standard signal identifier when the signal determination identifier is the red light single detection identifier;

Step 5 comprises: Step 51, a temporary first determination result is initialized to be null;

Step 52, whether the signal determination identifier is the red and green light dual detection identifier is determined; when the signal determination identifier is the red and green light dual detection identifier, Step 53 is performed; or, when the signal determination identifier is a red light single detection identifier, Step 55 is performed;

Here, if the signal determination identifier is specifically set as the red and green dual detection identifier, it indicates that the photographing device currently used for photographing can process red and green lights normally, and Step 53 will be performed to determine the signal quality of the second red light digital signal and the second green light digital signal through associated detection of a frequency difference between the second red light digital signal and the second green light digital signal; if the signal determination identifier is specifically set as the red light single detection identifier, it indicates that the photographing device currently used for photographing has a poor capacity to process green light, the second green light digital signal will be abandoned in the subsequent light signal processing process, that is, the second green light digital signal will not be used for maximum frequency difference determination, and in order to make the whole process to be performed continuously, Step 55 will be performed to directly set the first determination result as the up-to-standard identifier without frequency difference comparison of red and green lights;

Step 53, digital signal time domain-frequency domain conversion is performed on the second red light digital signal through discrete Fourier transform to generate a red light frequency domain signal, and digital signal time domain-frequency domain conversion is performed on the second green light digital signal through discrete Fourier transform to generate a green light frequency domain signal; an maximum-energy frequency is extracted from the red light frequency domain signal to generate a maximum red light frequency, and an maximum-energy frequency is extracted from the green light frequency domain signal to generate a maximum green light frequency; and a maximum red-green frequency difference is generated according to a frequency difference between the maximum red light frequency and the maximum green light frequency;

Step 54, signal maximum frequency difference determination is performed on the maximum red-green frequency difference according to a preset maximum frequency difference threshold range; when the maximum red-green frequency difference does not exceed the maximum frequency difference threshold range, the temporary first determination result is set as the up-to-standard signal identifier; or, when the maximum red-green frequency difference exceeds the maximum frequency difference threshold range, the temporary first determination result is set as the not-up-to-standard signal identifier; and Step 56 is performed;

Here, frequency domain signals of the second red light digital signal and the second green light digital signal are obtained through discrete Fourier transform first; maximum-energy frequencies are obtained according to the frequency domain signals (generally, this frequency corresponds to the heart rate); whether the maximum-energy frequencies of the two digital signals are consistent is checked; if an error is within an allowable error range, analysis is performed continuously; or, if the error is large, the signal quality is poor, and photographing is performed again;

Step 55, the temporary first determination result is set as the up-to-standard signal identifier;

Here, as described above, considering that the quality of green digital signals in skin surface video data acquired by some mobile terminals is poor, in order to guarantee the compatibility with different mobile terminals, the signal determination identifier is set as the red light single detection identifier to skip the process of detecting the signal quality based on the frequency difference;

Step 56, the first determination result is set as the temporary first determination result.

Step 6, when the first determination result is the up-to-standard signal identifier, signal-to-noise ratio determination is performed on the second red light digital signal and/or the second green light digital signal according to the signal determination identifier to generate a second determination result;

Step 6 comprises: Step 60, a temporary second determination result is initialized to be null;

Step 61, when the first determination result is the up-to-standard signal identifier, determination is performed according to the signal determination identifier; when the signal determination identifier is the red and green light dual detection identifier, Step 62 is performed; or, when the signal determination identifier is the red light single detection identifier, Step 65 is performed;

Here, if the signal determination identifier is specifically set as the red and green dual detection identifier, it indicates that the photographing device currently used for photographing can process red and green lights normally, and Step 62 will be performed to further determine the signal quality of the second red light digital signal and the second green light digital signal by comparing the signal-to-noise ratios of the second red light digital signal and the second green light digital signal with a preset threshold; if the signal determination identifier is specifically set as the red light single detection identifier, it indicates that the photographing device currently used for photographing has a poor capacity to process green light, the second green light digital signal will be abandoned in the subsequent light signal processing process, and Step 65 will be performed to further determine the signal quality of the second red light digital signal by comparing the signal-to-noise ratio of the second red light digital signal with a preset threshold;

Step 62, multi-order Butterworth band-stop filtering processing is performed on the second red light digital signal according to a preset band-stop filtering frequency threshold range, and valid signals with a signal frequency meeting the band-stop filtering frequency threshold range are filtered out of the second red light digital signal to generate a red light noise signal; and multi-order Butterworth band-stop filtering processing is performed on the second green light digital signal according to the preset band-stop filtering frequency threshold range, and valid signals with a signal frequency meeting the band-stop filtering frequency threshold range are filtered out of the second green light digital signal to generate a green light noise signal;

Step 63, signal energy of the second red light digital signal is calculated to generate red light signal energy, signal energy of the red light noise signal is calculated to generate red light noise energy, valid red light signal energy is generated according to a difference between the red light signal energy and the red light noise energy, and a red light signal-to-noise ratio is generated according to a ratio of the valid red light signal energy to the red light noise energy; signal energy of the second green light digital signal is calculated to generate green light signal energy, signal energy of the green light noise signal is calculated to generate green light noise energy, valid green light signal energy is generated according to a difference between the green light signal energy and the green light noise energy, and a green light signal-to-noise ratio is generated according to a ratio of the valid green light signal energy to the green light noise energy;

Step 64, if the red light signal-to-noise ratio and the green light signal-to-noise ratio are both less than a preset signal-to-noise threshold, the temporary second determination result is set as the not-up-to-standard signal identifier; or, if any one of the red light signal-to-noise ratio and the green light signal-to-noise ratio is greater than or equal to the signal-to-noise threshold, the temporary second determination result is set as the up-to-standard signal identifier; and Step 67 is performed;

Herein, in Step 62-Step 64, secondary filtering is performed on red and green lights: the secondary filtering is band-stop filtering, that is, signals within the band-stop filtering frequency threshold range are restrained. Specifically, multi-order Butterworth band-stop filtering (such as, four-order Butterworth band-stop filtering, three-order Butterworth band-stop filtering, two-order Butterworth band-stop filtering, or one-order Butterworth band-stop filtering) is used to filter out valid signals and reserve noise and interference signals to generate nose signals; next, energy of the valid signals and energy of the noise signals are calculated to generate signal-to-noise ratios; and finally, whether the signal quality of the red and green digital signals is up to standard is recognized according to a preset threshold of signal-to-noise ratio;

Step 65, multi-order Butterworth band-stop filtering processing is performed on the second red light digital signal according to the band-stop filtering frequency threshold range, valid signals with a signal frequency meeting the band-stop filtering frequency threshold range are filtered out of the second red light digital signal to generate the red light noise signal; the signal energy of the second red light digital signal is calculated to generate the red light signal energy, the signal energy of the red light noise signal is calculated to generate the red light noise energy, the valid red signal energy is generated according to the difference between the red light signal energy and the red light noise energy, and the red light signal-to-noise ratio is generated according to the ratio of the valid red light signal energy to the red light noise energy;

Step 66, if the red light signal-to-noise ratio is less than the signal-to-noise threshold, the temporary second determination result is set as the not-up-to-standard signal identifier; or, if the red light signal-to-noise ratio is greater than or equal to the signal-to-noise threshold, the temporary second determination result is set as the up-to-standard signal identifier;

Here, in Step 65-Step 66, considering that the quality of green digital signals in skin surface video data acquired by some mobile terminals is poor, the signal determination identifier is set as the red light single detection identifier, so secondary filtering is only performed on red light, valid signals are filtered through band-stop filtering, and noise and interference signals are reserved to generate a red light noise signal; next, the energy of the valid signals and the energy of the noise signal are calculated to generate a red light signal-to-noise ratio; and finally, whether the signal quality of the red light digital signal is up to standard is recognized according to a preset signal-to-noise ratio threshold;

Step 67, the second determination result is set as the temporary second determination result.

Step 7, when the second determination result is the up-to-standard signal identifier, PPG signal generation is performed on the second red light digital signal and/or the second green light digital signal according to the signal determination identifier to generate a PPG signal;

Step 7 comprises: Step 71, when the second determination result is the up-to-standard signal identifier, the PPG signal is set to be null, a channel identifier of the PPG signal is initialized to be null, a red light digital signal of the PPG signal is initialized to be null, and a green light digital signal of the PPG signal is initialized to be null;

Step 72, when the signal determination identifier is the red and green light dual detection identifier, the channel identifier of the PPG signal is set as a red and green channel identifier, the red light digital signal of the PPG signal is set as the second red light digital signal, and the green light digital signal of the PPG signal is set as the second green light digital signal;

Step 73, when the signal determination identifier is the red light single detection identifier, the channel identifier is set as a red channel identifier, and the red light digital signal of the PPG signal is set as the second red light digital signal.

Here, the PPG signal comprises the channel identifier, the red light digital signal and the green light digital signal.

Here, if the signal determination identifier is the red and green light dual detection identifier, it indicates that the capacity to process red and green lights of the mobile terminal used for acquisition and photographing is qualified, and the channel identifier will be set as the red and green channel identifier, which indicates that the PPG signal comprises two light digital signals (or two types of channel data); if the signal determination identifier is the red light single detection identifier, it indicates that the capacity to process green light of the mobile terminal used for acquisition and photographing is unqualified, the channel identifier will be set as the red channel identifier, which indicates that the PPG signal comprises only one light digital signal (or only one type of channel data).

Figure 2:
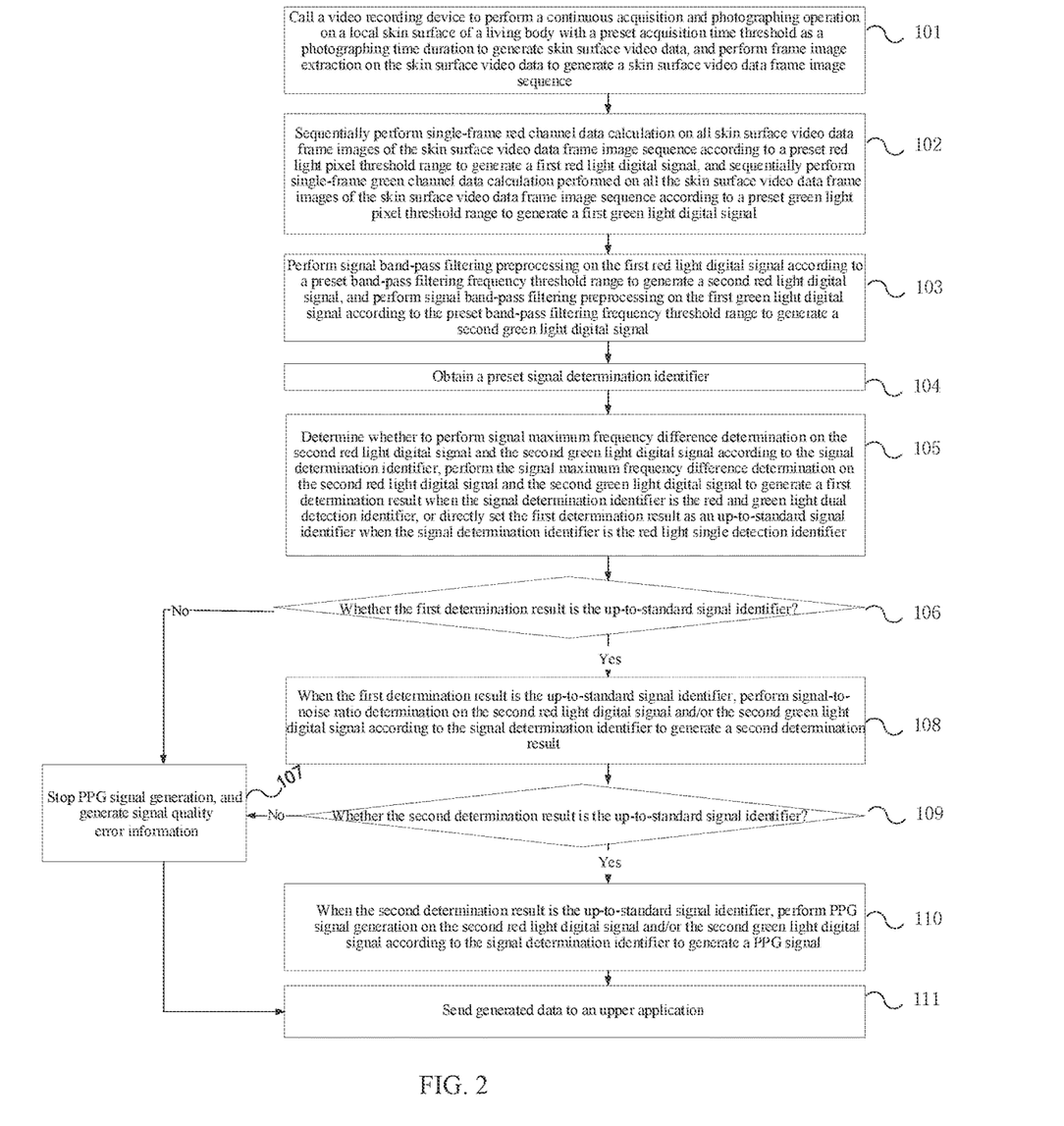
FIG. 2 is a schematic diagram of a method for generating PPG signals according to Embodiment 2 of the disclosure.

As shown in FIG. 2, which is a schematic diagram of a method for generating PPG signals according to Embodiment 2 of the disclosure, the method mainly comprises the following steps:

Step 101, a video recording device is called to perform a continuous acquisition and photographing operation on a local skin surface of a living body with a preset acquisition time threshold as a photographing time duration to generate skin surface video data; and frame image extraction is performed on the skin surface video data to generate a frame image sequence of skin surface video data;

Wherein, the frame image sequence of skin surface video data comprises multiple skin surface video data frame images;

Here, any mobile terminals provided with a camera and having a video recording function in daily life may be used as the video recording device in this embodiment of the disclosure; before photographing, a flashlight of the mobile terminal is turned on and is kept on normally to meet the requirement for a stable illuminating light source; during photographing, the local skin surface of the photographed living body should be slightly pressed against the camera of the mobile terminal; if the flashlight and the camera of the mobile terminal are close to each other, the skin surface covers both the flashlight and the camera; or, if the flashlight and the camera of the mobile terminal are away from each other, the skin surface only covers the camera; during the photographing process, the skin surface should be kept static, and force should be applied uniformly to the skin surface; and the acquisition time threshold may be predefined repeatedly according to the data storage capacity and analysis capacity of an actual application.

Step 102, single-frame red channel data calculation is sequentially performed on frame images of all skin surface video data frame images in the frame image sequence of skin surface video data according to a preset red light pixel threshold range to generate a first red light digital signal, and single-frame green channel data calculation is sequentially performed on frame images of all the skin surface video data in the frame image sequence of skin surface video data according to a preset green light pixel threshold range to generate a first green light digital signal.

Here, in Embodiment 2, information of various lights (only red light and green light in this embodiment) in all the frame images in the frame image sequence converted from skin surface video data is extracted in Step 102; as for the extraction of light signals, weighted average calculation is performed on specific pixels in the frame image to obtain a pixel average that is used to represent the color channel data of the corresponding light in the frame image; and each frame image in the video is processed in the same way in chronological order to obtain two segments of one-dimensional digital signals: first red light digital signal and first green light digital signal.

Step 103, signal band-pass filtering preprocessing is performed on the first red light digital signal according to a preset band-pass filtering frequency threshold range to generate a second red light digital signal, and signal band-pass filtering preprocessing is performed on the first green light digital signal according to the preset band-pass filtering frequency threshold range to generate a second green light digital signal.

Here, Step 103, signal preprocessing, namely denoising, is performed on the two light digital signals extracted according to the video data. In Embodiment 1, band-pass filtering is used for denoising, that is, a band-pass filtering frequency threshold range is preset, and signals, interference and noise lower or higher than the band-pass filtering frequency threshold range are restrained based on the band-pass filtering principle. Generally, the band-pass filtering frequency threshold range is 0.5-10 THz. When some mobile terminals are used for band-pass filtering, considering the processing capacity of the mobile terminals, a finite impulse response (FIR) filtering module is used.

Step 104, a preset signal determination identifier is obtained;

Wherein, the preset signal determination identifier is a red and green light dual detection identifier or a red light single detection identifier;

Here, the signal determination identifier is set and determined for the purpose of improving the compatibility with the photographing device. In some specific application scenarios, some mobile terminals have a poor capacity to process green light due to poor lens quality, equipment aging, an undeveloped polarization algorithm or other reasons, a sufficient quantity of pixel information with pixel values up to standard cannot be obtained from video data and even frame image data of videos acquired through these mobile terminals, and thus, a green light digital signal cannot be generated. In this case, the signal determination identifier is set to handle different cases flexibly: red and green light dual detection means that both red and green signals need to be recognized, and red light single detection means that only a red light signal needs to be recognized.

Step 105, whether to perform signal maximum frequency difference determination on the second red light digital signal and the second green light digital signal is determined according to the signal determination identifier, the signal maximum frequency difference determination is performed on the second red light digital signal and the second green light digital signal to generate a first determination result when the signal determination identifier is the red and green light dual detection identifier, or the first determination result is directly set as an up-to-standard signal identifier when the signal determination identifier is the red light single detection identifier;

Step 105 comprises: Step 1051: a temporary first determination result is initialized to be null;

Step 1052, whether the signal determination identifier is the red and green light dual detection identifier is determined; when the signal determination identifier is the red and green light dual detection identifier, Step 1053 is performed; or, when the signal determination identifier is a red light single detection identifier, Step 1055 is performed;

Here, if the signal determination identifier is specifically set as the red and green dual detection identifier, it indicates that the photographing device currently used for photographing can process red and green light normally, and Step 1053 will be performed to determine the signal quality of the second red light digital signal and the second green light digital signal through associated detection of a frequency difference between the second red light digital signal and the second green light digital signal; if the signal determination identifier is specifically set as the red light single detection identifier, it indicates that the photographing device currently used for photographing has a poor capacity to process green light, the second green light digital signal will be abandoned in the subsequent light signal processing process, that is, the second green light digital signal will not be used for maximum frequency difference determination, and in order to make the whole process to be performed continuously, Step 1055 will be performed to directly set the first determination result as the up-to-standard identifier without frequency difference comparison of red and green lights;

Step 1053, digital signal time domain-frequency domain conversion is performed on the second red light digital signal through discrete Fourier transform to generate a red light frequency domain signal, and digital signal time domain-frequency domain conversion is performed on the second green light digital signal through discrete Fourier transform to generate a green light frequency domain signal; an maximum-energy frequency is extracted from the red light frequency domain signal to generate a maximum red light frequency, and an maximum-energy frequency is extracted from the green light frequency domain signal to generate a maximum green light frequency; and a maximum red-green frequency difference is generated according to a frequency difference between the maximum red light frequency and the maximum green light frequency;

Step 1054, signal maximum frequency difference determination is performed on the maximum red-green frequency difference according to a preset maximum frequency difference threshold range; when the maximum red-green frequency difference does not exceed the maximum frequency difference threshold range, the temporary first determination result is set as the up-to-standard signal identifier; or, when the maximum red-green frequency difference exceeds the maximum frequency difference threshold range, the temporary first determination result is set as the not-up-to-standard signal identifier; and Step 1056 is performed;

Here, frequency domain signals of the second red light digital signal and the second green light digital signal are obtained through discrete Fourier transform first; maximum-energy frequencies are obtained according to the frequency domain signals (generally, this frequency corresponds to the heart rate); whether the maximum-energy frequencies of the two digital signals are consistent is checked; if an error is within an allowable error range, analysis is performed continuously; or, if the error is large, the signal quality is poor, and photographing is performed again;

Step 1055, the temporary first determination result is set as the up-to-standard signal identifier;

Here, as described above, considering that the quality of green digital signals in skin surface video data acquired by some mobile terminals is poor, in order to guarantee the compatibility with different mobile terminals, the signal determination identifier is set as the red light single detection identifier to skip the process of detecting the signal quality based on the frequency difference;

Step 1056, the first determination result is set as the temporary first determination result.

Step 106, whether the first determination result is the up-to-standard signal identifier is determined; if the first determination result is a not-up-to-standard signal identifier, Step 107 is performed; or, if the first determination result is the up-to-standard signal identifier, Step 108 is performed.

Here, when the first determination result is the not-up-to-standard signal identifier, Step 107 is performed to stop PPG signal analysis instantly and generate signal quality error information, which will be sent to an upper application, and the upper application determines whether to remind users to re-photograph the skin surface actively or automatically; or, when the first determination result is the up-to-standard signal identifier, Step 108 is performed to further determine the quality of the signals.

Step 107, PPG signal generation is stopped, and signal quality error information is generated; and Step 111 is performed.

Step 108, when the first determination result is the up-to-standard signal identifier, signal-to-noise ratio determination is performed on the second red light digital signal and/or the second green light digital signal according to the signal determination identifier to generate a second determination result;

Step 108 comprises: Step 1080, a temporary second determination result is initialized to be null;

Step 1081, when the first determination result is the up-to-standard signal identifier, determination is performed according to the signal determination identifier; when the signal determination identifier is the red and green light dual detection identifier, Step 1082 is performed; or, when the signal determination identifier is the red light single detection identifier, Step 1085 is performed;

Here, if the signal determination identifier is specifically set as the red and green dual detection identifier, it indicates that the photographing device currently used for photographing can process red and green light normally, and Step 1082 will be performed to further determine the signal quality of the second red light digital signal and the second green light digital signal by comparing the signal-to-noise ratios of the second red light digital signal and the second green light digital signal with a preset threshold; if the signal determination identifier is specifically set as the red light single detection identifier, it indicates that the photographing device currently used for photographing has a poor capacity to process green light, the second green light digital signal will be abandoned in the subsequent light signal processing process, and Step 1085 will be performed to further determine the signal quality of the second red light digital signal by comparing the signal-to-noise ratio of the second red light digital signal with a preset threshold;

Step 1082, multi-order Butterworth band-stop filtering processing is performed on the second red light digital signal according to a preset band-stop filtering frequency threshold range, and valid signals with a signal frequency meeting the band-stop filtering frequency threshold range are filtered out of the second red light digital signal to generate a red light noise signal; and multi-order Butterworth band-stop filtering processing is performed on the second green light digital signal according to the preset band-stop filtering frequency threshold range, and valid signals with a signal frequency meeting the band-stop filtering frequency threshold range are filtered out of the second green light digital signal to generate a green light noise signal;

Step 1083, signal energy of the second red light digital signal is calculated to generate red light signal energy, signal energy of the red light noise signal is calculated to generate red light noise energy, valid red light signal energy is generated according to a difference between the red light signal energy and the red light noise energy, and a red light signal-to-noise ratio is generated according to a ratio of the valid red light signal energy to the red light noise energy; signal energy of the second green light digital signal is calculated to generate green light signal energy, signal energy of the green light noise signal is generated to generate green light noise energy, valid green light signal energy is generated according to a difference between the green light signal energy and the green light noise energy, and a green light signal-to-noise ratio is generated according to a ratio of the valid green light signal energy to the green light noise energy;

Step 1084, if the red light signal-to-noise ratio and the green light signal-to-noise ratio are both less than a preset signal-to-noise threshold, the temporary second determination result is set as the not-up-to-standard signal identifier; or, if any one of the red light signal-to-noise ratio and the green light signal-to-noise ratio is greater than or equal to the signal-to-noise threshold, the temporary second determination result is set as the up-to-standard signal identifier; and Step 1087 is performed;

Here, in Step 1082-Step 1084, secondary filtering is performed on red and green lights: the secondary filtering is band-stop filtering, that is, signals within the band-stop filtering frequency threshold range are restrained. Specifically, multi-order Butterworth band-stop filtering (such as, four-order Butterworth band-stop filtering, three-order Butterworth band-stop filtering, two-order Butterworth band-stop filtering, or one-order Butterworth band-stop filtering) is used to filter out valid signals and reserve noise and interference signals to generate nose signals; next, energy of the valid signals and energy of the noise signals are calculated to generate signal-to-noise ratios; and finally, whether the signal quality of the red and green digital signals is up to standard is recognized according to a preset signal-to-noise ratio threshold;

Step 1085, multi-order Butterworth band-stop filtering processing is performed on the second red light digital signal according to the band-stop filtering frequency threshold range, valid signals with a signal frequency meeting the band-stop filtering frequency threshold range are filtered out of the second red light digital signal to generate the red light noise signal; the signal energy of the second red light digital signal is calculated to generate the red light signal energy, the signal energy of the red light noise signal is calculated to generate the red light noise energy, the valid red signal energy is generated according to the difference between the red light signal energy and the red light noise energy, and the red light signal-to-noise ratio is generated according to the ratio of the valid red light signal energy to the red light noise energy;

Step 1086, if the red light signal-to-noise ratio is less than the signal-to-noise threshold, the temporary second determination result is set as the not-up-to-standard signal identifier; or, if the red light signal-to-noise ratio is greater than or equal to the signal-to-noise threshold, the temporary second determination result is set as the up-to-standard signal identifier;

Here, in Step 1085-Step 1086, considering that the quality of green digital signals in skin surface video data acquired by some mobile terminals is poor, the signal determination identifier is specifically set as the red light single detection identifier, so secondary filtering is only performed on red light, valid signals are filtered through band-stop filtering, and noise and interference signals are reserved to generate a red light noise signal; next, the energy of the valid signals and the energy of the noise signal are calculated to generate a red light signal-to-noise ratio; and finally, whether the signal quality of the red light digital signal is up to standard is recognized according to a preset signal-to-noise ratio threshold;

Step 1087, the second determination result is set as the temporary second determination result.

Step 109, whether the second determination result is the up-to-standard signal identifier is determined; if the second determination result is the not-up-to-standard signal identifier, Step 107 is performed; or, if the second determination result is the up-to-standard signal identifier, Step 110 is performed.

Here, when the second determination result is the not-up-to-standard signal identifier, Step 107 is performed to stop PPG signal analysis instantly and generate signal quality error information, which will be sent to an upper application, and the upper application determines whether to remind users to re-photograph the skin surface actively or automatically; or, when the second determination result is the up-to-standard signal identifier, Step 110 is performed to set a finally generated PPG signal.

Step 110, when the second determination result is the up-to-standard signal identifier, PPG signal generation is performed on the second red light digital signal and/or the second green light digital signal according to the signal determination identifier to generate a PPG signal;

Step 110 comprises: Step 1101, when the second determination result is the up-to-standard signal identifier, the PPG signal is set to be null, a channel identifier of the PPG signal is initialized to be null, a red light digital signal of the PPG signal is initialized to be null, and a green light digital signal of the PPG signal is initialized to be null;

Step 1102, when the signal determination identifier is the red and green light dual detection identifier, the channel identifier of the PPG signal is set as a red and green channel identifier, the red light digital signal of the PPG signal is set as the second red light digital signal, and the green light digital signal of the PPG signal is set as the second green light digital signal;

Step 1103, when the signal determination identifier is the red light single detection identifier, the channel identifier is set as a red channel identifier, and the red light digital signal of the PPG signal is set as the second red light digital signal.

Here, the PPG signal comprises the channel identifier, the red light digital signal and the green light digital signal.

Here, if the signal determination identifier is the red and green light dual detection identifier, it indicates that the capacity to process red and green lights of the mobile terminal used for acquisition and photographing is qualified, and the channel identifier will be set as the red and green channel identifier, which indicates that the PPG signal comprises two light digital signals (or two types of channel data); if the signal determination identifier is the red single detection identifier, it indicates that the capacity to process green light of the mobile terminal used for acquisition and photographing is unqualified, the channel identifier will be set as the red channel identifier, which indicates that the PPG signal comprises only one light digital signal (or only one type of channel data).

Step 111, generated data is sent to an upper application.

Here, data directly generated from Step 107 is specifically the signal quality error information, and data directly generated from Step 110 is specifically the PPG signal.

Figure 3:
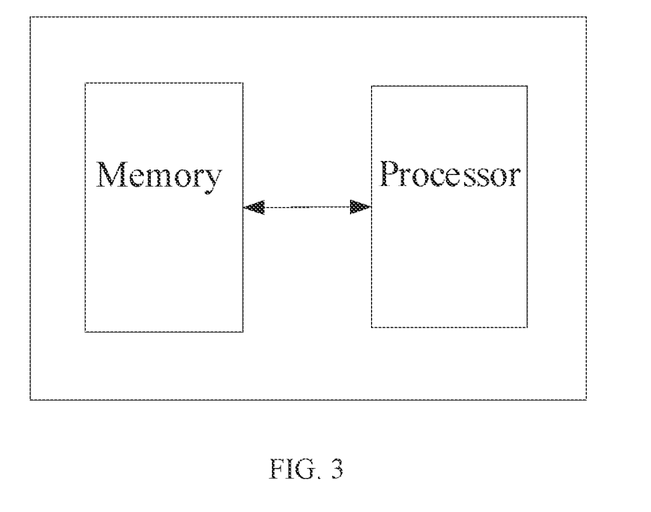
FIG. 3 is a structural diagram of a device for generating PPG signals according to Embodiment 3 of the disclosure.

FIG. 3 is a structural diagram of a device for generating PPG signals provided by Embodiment 3 of the disclosure. Equipment comprises a processor and a memory. The memory may be connected to the processor through a bus. The memory may be a nonvolatile memory such as a hard disk drive and a flash memory, and a software program and an equipment drive program are stored in the memory. The software program can implement all functions of the method provided by the embodiments of the disclosure, and the equipment drive program may be a network and interface drive program. The processor is used to execute the software program, and when the software program is executed, the method provided by the embodiments of the disclosure is implemented.

It should be noted that the embodiments of the disclosure further provide a computer-readable storage medium having a computer program stored therein, and when the computer program is executed by a processor, the method provided by the embodiments of the disclosure is implemented.

The embodiments of the disclosure further provide a computer program product comprising instructions. When the computer program product runs on a computer, a processor implements the method mentioned above.

The embodiments of the disclosure provide a method and device for generating PPG signals. By adoption of the method provided by the embodiments of the disclosure, the type of a radiation source is not specified, so common lamplight may be adopted; a PPG signal front-end acquisition device is simplified, and a common mobile terminal may be used; recorded video data is analyzed to generate a PPG signal, which not only meets the requirements for real-time analysis and data backup of local equipment, but also meets the requirements for remote transmission and analysis; valid signals may be recognized independent of specific sensors, so the PPG data acquisition difficult is lowered for an application layer; and a signal determination identifier is set to improve the compatibility with various photographing devices.

Those skilled should further appreciate that the units and arithmetic steps described in conjunction with the embodiments in this specification may be implemented by electronic hardware, computer software, or a combination of these two. To clearly explain the interchangeability of hardware and software, the components and steps of illustrative embodiments have been generally described according to their functions. Whether these functions are implemented by hardware or software depends on specific applications and design constraints of the technical solutions. For each specific application, those skilled may implement these functions in different ways, which should not be construed as exceeding the scope of the disclosure.

The steps of the method or algorithm described in the embodiments in this specification may be implemented by hardware, software modules executed by a processor, or a combination of these two. The software modules may be configured in a random access memory (RAM), a memory, a read-only memory (ROM), an electrically programmable ROM, an electrically erasable and programmable ROM, a register, a hard disk, a removable disk, a CD-ROM, or a storage medium in any other forms in the art.

The purposes, technical solutions and beneficial effects of the embodiments of the disclosure are described in further detail with reference to the above specific implementations. It should be understood that the above implementations are merely specific ones of the disclosure, and are not used to limit the protection scope of the invention as recited in the claims. Any amendments, equivalent substitutions, and improvements made based on the spirit and principle of the disclosure should also fall within the protection scope of the invention as recited in the claims.

What is claimed is:

1. A method for generating Photoplethysmography (PPG) signals, comprising:
    sequentially performing single-frame red channel data calculation on all skin surface video data frame images of a frame image sequence of the skin surface video data according to a preset red light pixel threshold range to generate a first red light digital signal, and sequentially performing single-frame green channel data calculation on all the skin surface video data frame images of the frame image sequence of the skin surface video data according to a preset green light pixel threshold range to generate a first green light digital signal, wherein the frame image sequence of skin surface video data comprises multiple skin surface video data frame images;
    performing signal band-pass filtering preprocessing on the first red light digital signal according to a preset band-pass filtering frequency threshold range to generate a second red light digital signal, and performing signal band-pass filtering preprocessing on the first green light digital signal according to the preset band-pass filtering frequency threshold range to generate a second green light digital signal;
    obtaining a preset signal determination identifier, wherein the preset signal determination identifier is a red and green light dual detection identifier or a red light single detection identifier;
    determining, according to the preset signal determination identifier, whether to perform signal maximum frequency difference determination on the second red light digital signal and the second green light digital signal, performing the signal maximum frequency difference determination on the second red light digital signal and the second green light digital signal to generate a first determination result when the preset signal determination identifier is the red and green light dual detection identifier, or directly setting the first determination result as an up-to-standard signal identifier when the preset signal determination identifier is the red light single detection identifier;
    performing, when the first determination result is the up-to-standard signal identifier, signal-to-noise ratio determination on the second red light digital signal and/or the second green light digital signal according to the signal determination identifier to generate a second determination result; and
    performing, when the second determination result is the up-to-standard signal identifier, PPG signal generation on the second red light digital signal and/or the second green light digital signal according to the signal determination identifier to generate a PPG signal.

2. The method for generating PPG signals according to claim 1, wherein:
    the frame image sequence of the skin surface video data is generated by calling a video recording device to perform a continuous acquisition and photographing operation on a local skin surface of a living body with a preset acquisition time threshold as a photographing time duration to generate skin surface video data and then performing frame image extraction on the skin surface video data.

3. The method for generating PPG signals according to claim 2, wherein calling a video recording device to perform a continuous acquisition and photographing operation on a local skin surface of a living body with a preset acquisition time threshold as a photographing time duration to generate skin surface video data comprises:
    calling an illuminating module of the video recording device to provide illumination for the local skin surface of the living body, wherein the video recording device comprises the illuminating module and a video recording module, and the video recording module at least comprises a lens module;
    when a physical distance between the illuminating module and the lens module is less than or equal to a preset device distance threshold, covering the illuminating module and the lens module with the local skin surface of the living body; or, when the physical distance between the illuminating module and the lens module is greater than the device distance threshold, covering the lens module with the local skin surface of the living body; and
    calling the video recording module to perform the continuous acquisition and photographing operation on the local skin surface of the living body with the preset acquisition time threshold as the photographing time duration to generate the skin surface video data.

4. The method for generating PPG signals according to claim 2, wherein the method further comprises:
    in the process of calling the video recording device to perform the continuous acquisition and photographing operation on the local skin surface of the living body with the preset acquisition time threshold as the photographing time duration, performing continuous video fragment extraction on the video data acquired and photographed by the video recording device with a preset cached fragment time threshold as a fragment extraction length to generate multiple cached fragments;

extracting frame images from each of the multiple cached fragments and sorting all the extracted frame images in chronological order to generate a cached fragment frame image sequence, wherein each of the multiple cached fragments comprise multiple frame images;

performing red pixel proportion statistics on all cached fragment frame images of the cached fragment frame image sequence according to the red light pixel threshold range to generate a red proportion parameter, and performing noise pixel proportion statistics according to a preset noise pixel threshold range to generate a noise proportion parameter, wherein the cached fragment frame image sequence comprises multiple cached fragment frame images;

performing out-of-skin surface photographing error recognition determination on each of the multiple cached fragments according to the red proportion parameter, and when the red proportion parameter is less than a preset red proportion lower threshold, stopping the continuous acquisition and photographing operation, and generating out-of-skin surface photographing error information; and performing out-of-skin surface photographing error recognition determination on each of the multiple cached fragments according to the noise proportion parameter, and when the noise proportion parameter is greater than a preset noise proportion upper threshold, stopping the continuous acquisition and photographing operation, and generating the out-of-skin surface photographing error information.

5. The method for generating PPG signals according to claim 1, wherein:
the first determination result is the up-to-standard signal identifier or a not-up-to-standard signal identifier; and
the second determination result is the up-to-standard signal identifier or the not-up-to-standard signal identifier.

6. The method for generating PPG signals according to claim 5, wherein the step of determining, according to the signal determination identifier, whether to perform signal maximum frequency difference determination on the second red light digital signal and the second green light digital signal, performing the signal maximum frequency difference determination on the second red light digital signal and the second green light digital signal to generate a first determination result when the signal determination identifier is the red and green light dual detection identifier, or directly setting the first determination result as an up-to-standard signal identifier when the signal determination identifier is the red light single detection identifier comprises:
a step B1, initializing a temporary first determination result to be null;
a step B2, determining whether the signal determination identifier is the red and green light dual detection identifier; when the signal determination identifier is the red and green light dual detection identifier, performing a step B3; or, when the signal determination identifier is the red light single detection identifier, performing a step B5;
the step B3, performing digital signal time domain-frequency domain conversion on the second red light digital signal through discrete Fourier transform to generate a red light frequency domain signal, and performing digital signal time domain-frequency domain conversion on the second green light digital signal through discrete Fourier transform to generate a green light frequency domain signal; extracting an maximum-energy frequency from the red light frequency domain signal to generate a maximum red light frequency, and extracting an maximum-energy frequency from the green light frequency domain signal to generate a maximum green light frequency; and generating a maximum red-green frequency difference according to a frequency difference between the maximum red light frequency and the maximum green light frequency;
a step B4, performing signal maximum frequency difference determination on the maximum red-green frequency difference according to a preset maximum frequency difference threshold range; when the maximum red-green frequency difference does not exceed the maximum frequency difference threshold range, setting the temporary first determination result as the up-to-standard signal identifier; or, when the maximum red-green frequency difference exceeds the maximum frequency difference threshold range, setting the temporary first determination result as the not-up-to-standard signal identifier; and performing a step B6;
the step B5, setting the temporary first determination result as the up-to-standard signal identifier; and
the step B6, setting the first determination result as the temporary first determination result.

7. The method for generating PPG signals according to claim 5, wherein the step of performing, when the first determination result is the up-to-standard signal identifier, signal-to-noise ratio determination on the second red light digital signal and/or the second green light digital signal according to the signal determination identifier to generate a second determination result comprises:
a step C1, initializing a temporary second determination result to be null;
a step C2, when the first determination result is the up-to-standard signal identifier, performing determination according to the signal determination identifier; when the signal determination identifier is the red and green light dual detection identifier, performing a step C3; or, when the signal determination identifier is the red light single detection identifier, performing a step C6;
the step C3, performing multi-order Butterworth band-stop filtering processing on the second red light digital signal according to a preset band-stop filtering frequency threshold range, and filtering valid signals with a signal frequency meeting the band-stop filtering frequency threshold range out of the second red light digital signal to generate a red light noise signal; and performing multi-order Butterworth band-stop filtering processing on the second green light digital signal according to the preset band-stop filtering frequency threshold range, and filtering valid signals with a signal frequency meeting the band-stop filtering frequency threshold range out of the second green light digital signal to generate a green light noise signal;
a step C4, calculating signal energy of the second red light digital signal to generate red light signal energy, calculating signal energy of the red light noise signal to generate red light noise energy, generating valid red light signal energy according to a difference between the red light signal energy and the red light noise energy, and generating a red light signal-to-noise ratio according to a ratio of the valid red light signal energy to the red light noise energy; calculating signal energy of the second green light digital signal to generate green light signal energy, calculating signal energy of the green light noise signal to generate green light noise energy, generating valid green light signal energy according to a difference between the green light signal energy and the green light noise energy, and generating a green light signal-to-noise ratio according to a ratio of the valid green light signal energy to the green light noise energy;

a step C5, if the red light signal-to-noise ratio and the green light signal-to-noise ratio are both less than a preset signal-to-noise threshold, setting the temporary second determination result as the not-up-to-standard signal identifier; or, if any one of the red light signal-to-noise ratio and the green light signal-to-noise ratio is greater than or equal to the signal-to-noise threshold, setting the temporary second determination result as the up-to-standard signal identifier; and performing a step C8;

the step C6, performing multi-order Butterworth band-stop filtering processing on the second red light digital signal according to the band-stop filtering frequency threshold range, filtering valid signals with a signal frequency meeting the band-stop filtering frequency threshold range out of the second red light digital signal to generate the red light noise signal; calculating the signal energy of the second red light digital signal to generate the red light signal energy, calculating the signal energy of the red light noise signal to generate the red light noise energy, generating the valid red signal energy according to the difference between the red light signal energy and the red light noise energy, and generating the red light signal-to-noise ratio according to the ratio of the valid red light signal energy to the red light noise energy;

a step C7, if the red light signal-to-noise ratio is less than the signal-to-noise threshold, setting the temporary second determination result as the not-up-to-standard signal identifier; or, if the red light signal-to-noise ratio is greater than or equal to the signal-to-noise threshold, setting the temporary second determination result as the up-to-standard signal identifier; and the step C8, setting the second determination result as the temporary second determination result.

8. The method for generating PPG signals according to claim 1, wherein the step of sequentially performing single-frame red channel data calculation on all skin surface video data frame images of a frame image sequence of the skin surface video data according to a preset red light pixel threshold range to generate a first red light digital signal, and sequentially performing single-frame green channel data calculation on all the skin surface video data frame images of the frame image sequence of the skin surface video data according to a preset green light pixel threshold range to generate a first green light digital signal comprises:

a step A1 initializing a temporary first red light digital signal to be null, initializing a temporary first green light digital signal to be null, initializing a first index to 1, and initializing a first total number to be a total number of the skin surface video data frame images in the frame image sequence of the skin surface video data;

a step A2, extracting the skin surface video data frame image corresponding to the first index from the frame image sequence of the skin surface video data to generate a first-index skin surface video data frame image;

a step A3, collecting all pixels, meeting the red light pixel threshold range, in the first-index skin surface video data frame image according to the red light pixel threshold range to generate a red pixel set, and performing weighted average calculation on pixel values of all the pixels in the red pixel set through a designated weighted average method to generate first-index frame red channel data; and adding the first-index frame red channel data into the temporary first red light digital signal as red light signal point data;

a step A4, collecting all pixels, meeting the green light pixel threshold range, in the first-index skin surface video data frame image according to the green light pixel threshold range to generate a green pixel set, and performing weighted average calculation on pixel values of all the pixels in the green pixel set through a designated weighted average method to generate first-index frame green channel data; and adding the first-index frame green channel data into the temporary first green light digital signal as green light signal point data;

a step A5, increasing the first index by 1;

a step A6, determining whether the first index is greater than the first total number; if the first index is less than or equal to the first total number, performing the step step A2, or, if the first index is greater than the first total number, performing a step A7, and the step A7, setting the first red light digital signal as the temporary first red light digital signal; and setting the first green light digital signal as the temporary first green digital signal.

9. The method for generating PPG signals according to claim 1, wherein the step of performing signal band-pass filtering preprocessing on the first red light digital signal according to a preset band-pass filtering frequency threshold range to generate a second red light digital signal, and performing signal band-pass filtering preprocessing on the first green light digital signal according to the preset band-pass filtering frequency threshold range to generate a second green light digital signal comprises:

according to the band-pass filtering frequency threshold range, performing digital signal filtering processing on low-frequency noise signal points with a signal frequency lower than the band-pass filtering frequency threshold range and high-frequency noise signal points with a signal frequency higher than the band-pass filtering frequency threshold range in the first red light digital signal to generate the second red light digital signal; and according to the band-pass filtering frequency threshold range, performing digital signal filtering processing on low-frequency noise signal points with a signal frequency lower than the band-pass filtering frequency threshold range and high-frequency noise signal points with a signal frequency higher than the band-pass filtering frequency threshold range in the first green light digital signal to generate the second green light digital signal.

10. The method for generating PPG signals according to claim 1, wherein the step of performing, when the second determination result is the up-to-standard signal identifier, PPG signal generation on the second red light digital signal and/or the second green light digital signal according to the signal determination identifier to generate a PPG signal comprises:

when the second determination result is the up-to-standard signal identifier, setting the PPG signal to be null, initializing a channel identifier of the PPG signal to be null, initializing a red light digital signal of the PPG signal to be null, and initializing a green light digital signal of the PPG signal to be null;

when the signal determination identifier is the red and green light dual detection identifier, setting the channel identifier of the PPG signal as a red and green channel identifier, setting the red light digital signal of the PPG signal as the second red light digital signal, and setting the green light digital signal of the PPG signal as the second green light digital signal; or     when the signal determination identifier is the red light single detection identifier, setting the channel identifier as a red channel identifier, and setting the red light digital signal of the PPG signal as the second red light digital signal.

11. The method for generating PPG signals according to claim 1, wherein the method further comprises:

when the first determination result is the not-up-to-standard signal identifier, stopping the PPG signal generation, and generating signal quality error information; and     when the second determination result is the not-up-to-standard signal identifier, stopping the PPG signal generation, and generating signal quality error information.

12. An equipment, comprising a memory and a processor, wherein the memory is used to store a program, and the processor is used to implement the method according to claim 1.

13. A computer program product comprising instructions, enabling a computer to implement the method according to claim 1 when running on the computer.

14. A non-transitory computer-readable storage medium, comprising an instruction, wherein when the instruction runs on a computer, the computer implements the method according to claim 1.

\* \* \* \* \*

UNITED STATES PATENT AND TRADEMARK OFFICE
CERTIFICATE OF CORRECTION

PATENT NO. : 12,303,232 B2  
APPLICATION NO. : 17/904688  
DATED : May 20, 2025  
INVENTOR(S) : Zejian Wu and Jun Cao Page 1 of 1

It is certified that error appears in the above-identified patent and that said Letters Patent is hereby corrected as shown below:

On the Title Page

In ITEM (57) ABSTRACT, Lines 10-11, change "green light digital signals;" to --green light signals;--

In the Specification

Column 10, Line 29, change "threshold is 1 s, a video" to --threshold is 1s, a video--  
Column 10, Line 30, change "each is in the" to --each 1s in the--  
Column 10, Line 41, change "Assume the is video" to --Assume the 1s video--

In the Claims

Claim 8, Column 28, Lines 29-30, change "the step step A2," to --the step A2,--

Signed and Sealed this  
Second Day of September, 2025

Coke Morgan Stewart  
*Acting Director of the United States Patent and Trademark Office*